US008013157B2

(12) United States Patent
Mani et al.

(10) Patent No.: US 8,013,157 B2
(45) Date of Patent: Sep. 6, 2011

(54) SYNTHESIS OF UNSATURATED PIPERIDINES FROM PIPERIDONES WITH A SILYL REAGENT

(75) Inventors: Neelakandha S. Mani, San Diego, CA (US); Christie Morrill, Green Brook, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 274 days.

(21) Appl. No.: 12/517,846

(22) PCT Filed: Dec. 19, 2007

(86) PCT No.: PCT/US2007/025991
§ 371 (c)(1),
(2), (4) Date: Jun. 5, 2009

(87) PCT Pub. No.: WO2008/079255
PCT Pub. Date: Jul. 3, 2008

(65) Prior Publication Data
US 2010/0324292 A1    Dec. 23, 2010

Related U.S. Application Data

(60) Provisional application No. 60/875,926, filed on Dec. 20, 2006.

(51) Int. Cl.
*C07F 7/02* (2006.01)
(52) U.S. Cl. ........................................................ 546/14
(58) Field of Classification Search .................... 546/14
See application file for complete search history.

(56) References Cited

U.S. PATENT DOCUMENTS

| | | | | |
|---|---|---|---|---|
| 4,857,521 | A * | 8/1989 | Kurono et al. ................ | 514/206 |
| 2002/0132797 | A1 | 9/2002 | Kerwin et al. | |
| 2004/0171672 | A1 | 9/2004 | De Brabander et al. | |
| 2005/0288317 | A1 | 12/2005 | Yao et al. | |
| 2006/0058287 | A1 | 3/2006 | Axten et al. | |

OTHER PUBLICATIONS

Adlington et al. "Recent Applications of the Shapiro Reaction" Acc. Chem. Res. 1983 vol. 16 pp. 55-59.
Barbachyn et al. "Identification of Phenylisoxazolines As Novel and Viable Antibacterial Agents Active Against Gram-Positive Pathogens" J. Med. Chem. 2003, 46, 284-302.
Barnett et al. "Synthesis of Picenadol Via Metalloenamine Alkylation Methodology" J. Org. Chem. 1989 vol. 54 pp. 4795-4800.
Barth et al. "Synthesis of a Representative CIS/TRANS Pair of 4,5-Disubstituted Cyclopentenyllithium Reagents" J. Org. Chem. 1985, 50, 2438-2443.
Barrow et al "In Vitro and In Vivo Evaluation of Dihydropyrimidinone C-5 Amides As Potent and Selective Alpha1A Receptor Antagonists for the Treatment of Benign Prostatic Hyperplasia" J Med Chem 2000 vol. 43 pp. 2703-2718.
Berge et al "Pharmaceutical Salts" J Pharm Sci 1977 vol. 66 pp. 1-19.
Bica et al. "An Iron-Containing Ionic Liquid As Recyclable Catalyst for Aryl Grignard Cross-Coupling of Alkyl Halides" Org. Lett. 2006 vol. 8 pp. 733-735.
Billotte, S. "Synthesis of C-Substituted Cyclic Amines Using Azacycloalkyl Organozinc Reagents" Synlett 1998, vol. 4 pp. 379-380.
Boice et al. "An Efficient Synthesis of a Highly Functionalized 4-Arylpiperidine" Tetrahedron 2004 vol. 60 pp. 11367-11374.
Bursavich et al. "From Peptides to Non-Peptide Peptidomimetics: Design and Synthesis of New Piperidine Inhibitors of Aspartic Peptidases" Org. Lett. 2001 vol. 3 pp. 2317-2320.
Chamberlin et al. Lithioalkenes From Arenesulfonylhydrazones. In Organic Reactions; Paquette, L. A., Ed.; John Wiley & Sons, Inc., 1990; vol. 39, pp. 1-83.
Chamberlin et al. "Vinyllithium Reagents From Arenesulfonylhydrazones" J. Org. Chem. 1978, 43, 147-154.
Cody et al. "The Discovery and Preparation of Disubstituted Novel Amino-Aryl-Piperidine-Based Renin Inhibitors" Bioorg. Med. Chem. 2005 vol. 13 pp. 59-68.
Corley "Direct Synthesis of 4-Arylpiperidines Via Palladium/Copper(I)-Cocatalyzed Negishi Coupling of a 4-Piperidylzinc Iodide With Aromatic Halides and Triflates" J. Org. Chem. 2004 vol. 69 pp. 5120-5123.
Dantale et al. "A Novel Palladium-Catalyzed Synthesis of Beta-Carbolines: Application in Total Synthesis of Naturally Occurring Alkaloids" Tetrahedron 2003 vol. 59 pp. 5507-5514.
Denmark et al. "Total Synthesis of RK-397" J. Am. Chem. Soc. 2005 vol. 127 pp. 8971-8973.
Denmark et al. Organosilicon Compounds in Cross-Coupling Reactions. In Metal-Catalyzed Cross-Coupling Reactions, 2nd Ed.; De Meijere, A.; Diederich, F., Eds.; Wiley-VCH: Weinheim, 2004; pp. 163-216.
Denmark et al. "Cross-Coupling Reactions of Organosilicon Compounds: New Concepts and Recent Advances" Chem. Pharm. Bull. 2002 vol. 50 pp. 1531-1541.
Denmark et al. Acc. Chem. Res. "Design and Implementation of New, Silicon-Based, Cross-Coupling Reactions: Importance of Silicon-Oxygen Bonds" 2002 vol. 35 pp. 835-846.
Denmark et al. "Vinylation of Aryl Bromides Using an Inexpensive Vinylpolysiloxane" Org. Lett. 2006, 8, 63-66.
Eastwood, P. R. "A Versatile Synthesis of 4-Aryl Tetrahydropyridines Via Palladium Mediated Suzuki Cross-Coupling With Cyclic Vinyl Boronates" Tetrahedron Lett. 2000 vol. 41 pp. 3705-3708.
Filla et al "Novel Potent 5-HT1F Receptor Agonists: Structure-Activity Studies of a Series of Substituted N-(3-(1-Methyl-4-Piperidinyl)-1H-Pyrrolo(3,2-B)Pyridin-5-YL)amides" J. Med Chem 2003 vol. 46 pp. 3060-3071. Fonquerna et al., "Synthesis and Structure-Activity Relationships of Piperidinylpyrrolopyridine Derivatives As Potent and Selective H1 Antagonists" Bioorg. Med. Chem. Lett. 2005 vol. 15 pp. 1165-1167.
Greene, T. W.; Wuts, P. G. M. Protective Groups in Organic Synthesis, 2nd Ed.; John Wiley & Sons, Inc., 1991; pp. 441-452.
Guzikowski et al. "Synthesis of N-Substituted 4-(4-Hydroxyphenyl)Piperidines, 4-(4-Hydroxybenzyl)Piperidines, and (+−)-3-(4-Hydroxyphenyl)Pyrrolidines: Selective Antagonists At the 1A/2B NMDA Receptor Subtype" J. Med. Chem. 2000 vol. 43 pp. 984-994.
Huttenloch et al. "Solid-Phase Development of Chiral Phosphoramidite Ligands for Enantioselective Conjugate Addition Reactions" Chem. Eur. J. 2002, 8, 4767-4780.
Isaac et al "Design, Synthesis and Biological Activity of Novel Dimethyl-(2-(6-Substituted-Indol-1-YL)-Ethyl)-Amine As Potent, Selective, and Orally-Bioavailable 5-HT1D Agonists" Bioorg. Med. Chem. Lett. 2003, 13, 4409-4413.
Kiely et al. "Synthesis of 7-(Alkenyl, Cycloalkenyl, and 1,2,3,6-Thetrahydro-4-Pyridinyl)Quinolones" J. Heterocycl. Chem. 1991 vol. 28 pp. 1581-1585.
Larsen et al. "Synthesis of 4-Substituted Tetrahydropyridines by Cross-Coupling of Enol Phosphates" Tetrahedron Lett. 2005, vol. 46 pp. 4261-4263.

(Continued)

*Primary Examiner* — Charanjit Aulakh
(74) *Attorney, Agent, or Firm* — Michael J. Atkins

(57) ABSTRACT

Syntheses of unsaturated piperidines from piperidones through a silyl piperidine reagent via the Shapiro reaction and palladium-catalyzed cross-coupling reactions with organo halides.

29 Claims, No Drawings

OTHER PUBLICATIONS

Levell et al., "Structure based design of 4-(3-aminomethylphenyl)piperidinyl-1-amides: novel, potent, selective, and orally bioavailable inhibitors of beta II tryptase" Bioorg. Med. Chem. 2005, 13, 2859-2872.

Martin et al. "Synthesis of Spiro[Isobenzofuran-1(3H),4'-Piperidines] As Potential Central Nervous System Agents. 5. Conformationally Mobile Analogues Derived by Furan Ring Opening" J. Med. Chem. 1979 vol. 22 pp. 1347-1354.

Mewshaw et al. "Studies Toward the Discovery of the Next Generation of Antidepressants. Part 2: Incorporating a 5-HT1A Antagonist Component Into A Class of Serotonin Reuptake Inhibitors" Bioorg. Med. Chem. Lett. 2002 vol. 12 pp. 307-310.

Nakamura et al. E. "Iron-Catalyzed Chemoselective Cross-Coupling of Primary and Secondary Alkyl Halides With Arylzinc Reagents" Synlett 2005 vol. 11 pp. 1794-1798.

Paquette et al. "Silanes in Organic Synthesis. 8. Preparation of Vinylsilanes From Ketones and Their Regiospecific Cyclopentenone Annulation" J. Org. Chem. 1980, 45, 3017-3028.

Peterson et al. "Steroid Complexation by Cyclophane Receptors in Aqueous Solution: Substrate Selectivity, Enthalpic Driving Force for Cavity Inclusion, and Enthalpy-Entropy Compensation" Tetrahedron 1995 vol. 51 pp. 401-421.

Powell et al. "Nickel-Catalyzed Cross-Couplings of Organosilicon Reagents With Unactivated Secondary Alkyl Bromides" J. Am. Chem. Soc. 2004 vol. 126 pp. 7788-7789.

Quesnelle et al., "Biaryl Isoxazolinone Antibacterial Agents" Bioorg. Med. Chem. Lett. 2005, 15, 2728-2733.

Saari et al. "Adrenoceptor and Tetrabenazine Antagonism Activities of Some Pyridinyltetrahydropyridines" J. Med. Chem. 1984 vol. 27 pp. 1182-1185.

Sakamuri et al. "Pharmacophore-Based Discovery, Synthesis, and Biological Evaluation of 4-Phenyl-1-Arylalkyl Piperidines As Dopamine Transporter Inhibitors" Bioorg. Med. Chem. Lett. 2001, 11, 495-500.

Shapiro, R. H. Alkenes From Tosylhydrazones. In Organic Reactions; Dauben, W. G., Ed.; John Wiley & Sons, Inc., 1976; vol. 23 pp. 405-507.

Shkavrov et al. "A Convenient Synthesis of 1-Amino-7-(Piperidin-4-YL)Isoquinoline" Synth. Commun. 2005, vol. 35 pp. 725-730.

Scheiper et al. "Selective Iron-Catalyzed Cross-Coupling Reactions of Grignard Reagents With Enol Triflates, Acid Chlorides, and Dichloroarenes" J. Org. Chem. 2004 vol. 69 pp. 3943-3949.

Stahl & Wermuth Handbook of Pharmaceutical Salts, Properties, Selection and Use, Stahl and Wermuth Eds., Wiley-VCH and VHCA Zurich 2002.

Tan et al., "Estrogen Receptor Ligands. Part 5: The SAR of Dihydrobenzoxathiins Containing Modified Basic Side Chains" Bioorg. Med. Chem. Lett. 2004 vol. 14 pp. 3747-3751.

Trost et al. "Dinuclear Asymmetric ZN Aldol Additions: Formal Asymmetric Synthesis of Fostriecin" J. Am. Chem. Soc. 2005 vol. 127 pp. 3666-3667.

Trost et al. "Ruthenium-Catalyzed Vinylsilane Synthesis and Cross-Coupling As a Selective Approach to Alkenes: Benzyldimethylsilyl As a Robust Vinylmetal Functionality" Org. Lett. 2003 vol. 5 pp. 1895-1898.

Wenzel et al. "Structural Changes of Benzylether Derivatives of Vesamicol and Their Influence on the Binding Selectivity to the Vesicular Acetylcholine Transporter" Eur. J. Med. Chem. 2005 vol. 40 pp. 1197-12.

Wustrow et al. "Coupling of Arylboronic Acids With a Partially Reduced Pyridine Derivative" Synthesis 1991 vol. 11 pp. 993-995.

Zimmerman et al. "Characterization of the Neurotoxic Potential of M-Methoxy-MPTP and the Use of Its N-Ethyl Analogue As a Means of Avoiding Exposure To a Possible Parkinsonism-Causing Agent" J. Med. Chem 1986 vol. 29 pp. 1517-1520.

\* cited by examiner

SYNTHESIS OF UNSATURATED PIPERIDINES FROM PIPERIDONES WITH A SILYL REAGENT

CROSS-REFERENCE TO RELATED APPLICATIONS

This application is a national phase of International Application No. PCT/US2007/025991 and claims benefit of priority under 35 U.S.C. §119(e) of U.S. Provisional Application No. 60/875,926, filed on Dec. 20, 2006

FIELD OF THE INVENTION

The present invention is directed to novel processes for the preparation of unsaturated piperidines from piperidones through a silyl reagent. The Shapiro and palladium-catalyzed cross-coupling reactions with organo halides are employed.

BACKGROUND OF THE INVENTION

The present invention provides novel methodologies for the preparation of unsaturated piperidines, such as 3,4-unsaturated 4-arylpiperidines, from piperidones through silyl reagents via the Shapiro reaction and palladium-catalyzed cross-coupling reactions with organo halides, such as aryl iodides and bromides. Embodiments of this invention provide synthetic methodologies for making benzyl-protected, 3,4-unsaturated piperidine, which contains an aryldialkylalkenylsilane moiety, such as a benzyldimethylalkenylsilane moiety, from 1-benzyl-4-piperidone via the Shapiro reaction. This silyl piperidine readily undergoes palladium-catalyzed cross-coupling reactions with a variety of organo halides, such as aryl iodides and bromides, to generate 3,4-unsaturated piperidines, such as 3,4-unsaturated 4-arylpiperidines. Many of these coupling reactions according to this invention proceed at ambient temperature. These reactions present useful methods for 3,4-unsaturated piperidine and 4-arylpiperidine syntheses.

The 4-arylpiperidine moiety is commonly employed as a structural unit in numerous drug discovery programs, including those with potential application to the treatment of asthma,[1] hypertension,[2] depression,[3] migraine headaches,[4] bacterial infections,[5] prostrate gland enlargement,[6] estrogen-related disorders,[7] neurodegenerative disorders (e.g. Alzheimer's disease),[8] neuronal excitotoxicity (e.g. epilepsy, Parkinson's disease),[9] cocaine abuse,[10] and allergic rhinitis.[11] Both the 4-aryl group and the N-substituent are frequently used as points of structural diversification within such programs.[1,3c,4a,5,9,11]

Because relatively few 4-arylpiperidines are commercially available, new synthetic routes to obtain such compounds are desirable. The most common methods that are currently applied include the condensation of a 4-piperidone derivative with an anionic aryl species (Scheme 1, Eq. (1)),[3-4,8-12] the cross-coupling of a fully saturated piperidine reagent (Eq. (2)),[13] and the cross-coupling of a 3,4-unsaturated piperidine reagent (Eq. (3)).[1-2,5-7,14] The first of these three methods is often undesirable due to its harsh reaction conditions (i.e., strong nucleophiles and acids). The latter two methods are thus advantageous because they generally involve milder reaction conditions.

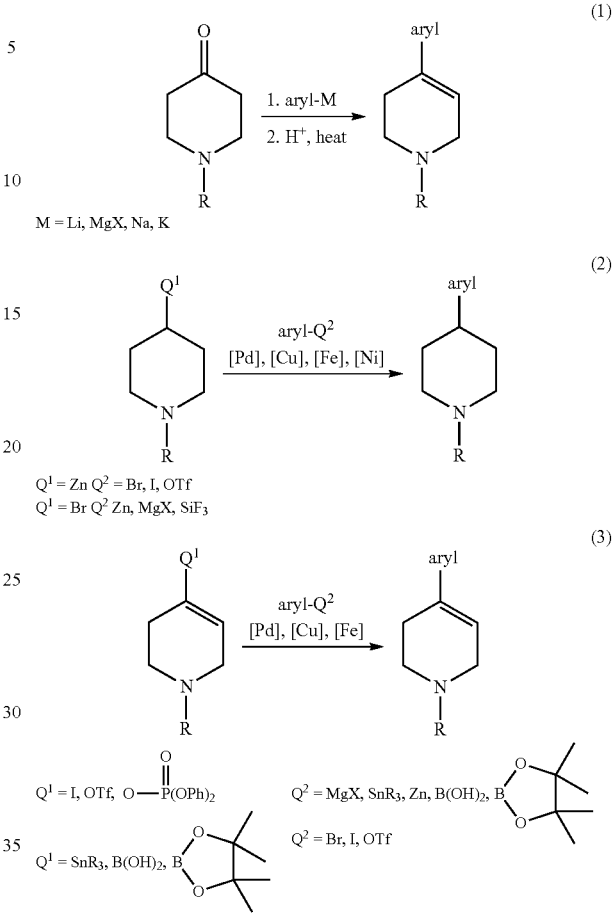

One disadvantage, however, that exists for the cross-coupling methods represented in Equations (2) and (3) is that the requisite piperidine reagents are generally not carried through multiple synthetic steps. They instead undergo the cross-coupling reaction immediately following their synthesis. Thus the manner in which a 4-arylpiperidine unit can be diversified within a drug discovery program is limited. This situation exists primarily because tin reagents introduce issues of toxicity and difficult by-product removal, while triflate, zinc, and boron reagents introduce issues of reagent instability and incompatibility.

Organosilanes have recently emerged as alternative cross-coupling reagents that possess the advantages of low toxicity and high stability.[15] Benzyldimethylsilyl reagents in particular exhibit notable stability toward acids and bases,[16] and they can be carried through multiple synthetic steps.[17] It was ascertained in the context of this invention whether a 3,4-unsaturated piperidine reagent containing a benzyldimethylsilyl moiety could be readily synthesized and successfully employed in the cross-coupling reaction represented in Equation (3). Some embodiments of this invention provide the application of the Shapiro reaction to efficiently convert 1-benzyl-4-piperidone into a benzyldimethylsilyl reagent. Other embodiments of this invention provide the use of palladium-catalyzed cross-coupling chemistry to subsequently transform this reagent into a variety of 3,4-unsaturated 4-arylpiperidines. Still other embodiments of this invention provide the application of the Shapiro reaction to efficiently convert 1-benzyl-4-piperidone into a benzyldimethylsilyl reagent and the use of palladium-catalyzed cross-coupling chemistry to subsequently transform this reagent into a variety of 3,4-unsaturated 4-arylpiperidines.

SUMMARY OF THE INVENTION

The present invention is directed to silyl compounds of formula (I):

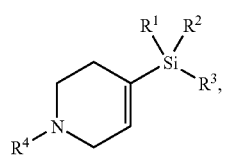

wherein
$R^1$ and $R^2$ are independently chosen from the group of alkyl, and alkyl substituted with at least one of halo, hydroxy, alkoxy, —COOH, and —COOAlkyl; $R^3$ is chosen from the group of H, Ar, heteroaryl, fluoro, hydroxyl, —OR$^1$, and —O—R$^5$;
$R^5$ is

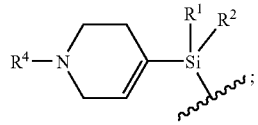

and
$R^4$ is chosen from the group of Ar, cycloalkyl, heterocycloalkyl, and heteroaryl, where $R^3$ and $R^4$ are independently optionally substituted with at least one of halo, hydroxy, alkoxy, —COOH, and —COOAlkyl;
and salts thereof.

The present invention is further directed to a process for the preparation of compounds of formula (I).

The present invention is further directed to a process for the preparation of 3,4-unsaturated piperidines with a silyl reagent of formula (I).

DETAILED DESCRIPTION OF THE INVENTION

The term "alkyl" or "Alkyl" refers to a straight- or branched-chain alkyl group having from 1 to 12 carbon atoms in the chain. Examples of alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

"Aryl", also "Ar" or "aryl", includes phenyl, also "Ph", naphthyl, biphenylyl, and tetrahydronaphthyl, any of which may be optionally substituted. Aryl also includes arylalkyl groups such as benzyl, phenethyl, and phenylpropyl.

The term "cycloalkyl" refers to a saturated or partially saturated, monocyclic, fused polycyclic, or Spiro polycyclic carbocycle having from 3 to 12 ring atoms per carbocycle. Illustrative examples of cycloalkyl groups include the following entities, in the form of properly bonded moieties:

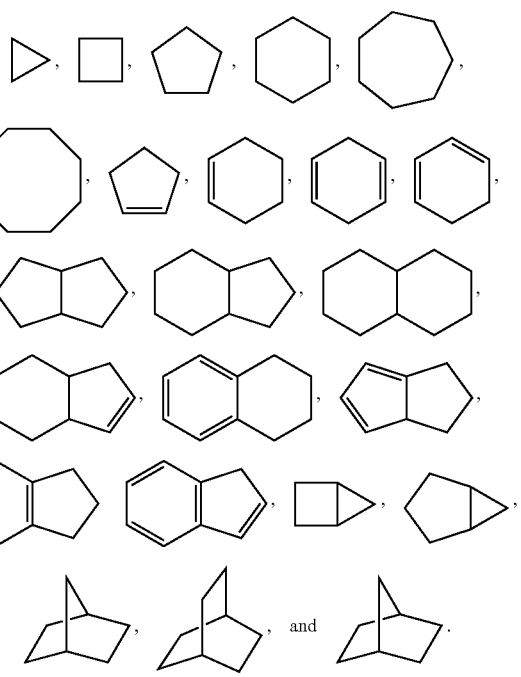

A "heterocycloalkyl" refers to a monocyclic, or fused, bridged, or Spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

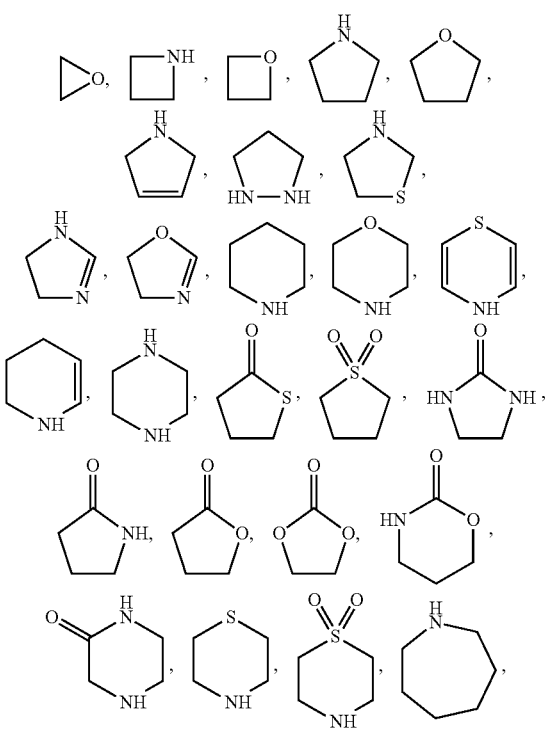

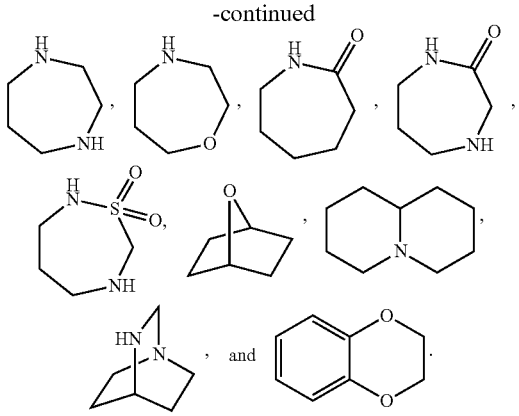

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

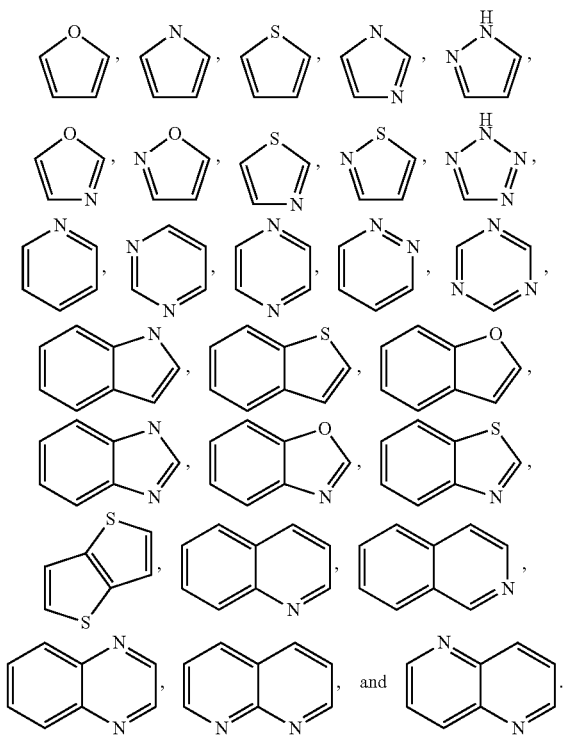

Those skilled in the art will recognize that the species of heteroaryl, cycloalkyl, and heterocycloalkyl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

To provide a more concise description, some of the quantitative expressions given herein are not qualified with the term "about" or the abbreviation "ca.". It is understood that, whether the term "about" or the abbreviation "ca." is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

To provide a more concise description, examples of media such as solvents, reaction media and crystallization media are provided by a list of embodiments of such media without reciting explicitly that further embodiments are exemplified by chemically compatible mixtures of the explicitly recited embodiments. It is understood that, whether the terms "and chemically compatible mixtures thereof" or "and mixtures thereof" are recited explicitly or not, such examples are also considered illustrative examples in the list.

Reference to a chemical entity herein by naming one of its forms stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COOH$^-$ upon dissociation in the medium being considered. In another example, an expression such as "exposing an entity to compound of formula R—COOH"

refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. In another example, a zwitterionic compound is encompassed herein by referring to a compound that is known to form a zwitterions, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Inerest (ChEBI) dictionary of molecular entities. (See, for example its on line version at http://www.ebi.ac.uk/chebi/init.do). As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labelled compounds are useful in metabolic studies (preferably with $^{14}$C), reaction kinetic studies (with, for example $^2$H or $^3$H), detection or imaging techniques (such as positron emission tomography (PET) or single-photon emission computed tomography (SPECT)) including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^{1-5}$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^{1-5}$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies $n \leq N \leq m$, with $m > n$, and equivalents thereof.

Any disubstituent referred to herein is meant to encompass the various attachment possibilities when more than one of such possibilities are allowed. For example, reference to disubstituent —A—B—, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

A "pharmaceutically acceptable salt" is intended to mean a salt of a free acid or base of a compound referred to herein that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound referred to herein in this context may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, halides, such as chlorides, bromides, and iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates. The term hydrohalide is used sometimes instead of halide.

If the compound referred to herein contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound referred to herein is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

Embodiments of this invention are provided by compounds of formula (I), wherein at least one of the following is satisfied:
$R^4$ is Ph-$CH_2$—;
$R^1$ is alkyl and $R^2$ is alkyl;
$R^1$ is methyl and $R^2$ is methyl;
$R^3$ is Ar;
$R^3$ is Ph-$CH_2$—;
$R^3$ is —O—$R^5$;
$R^1$ is alkyl, $R^2$ is alkyl, $R^3$ is Ph-$CH_2$—, and $R^4$ is Ph-$CH_2$—;
the salt is a hydrochloride salt; and
the salt is a hydrochloride salt.

Further embodiments of this invention are provided by processes for the preparation of a 3,4-unsaturated piperidine, comprising making a compound of formula (I) and salts thereof.

Still further embodiments of this invention are provided by such processes wherein at least one of the following is satisfied:
the compound of formula (I) is obtained by reacting a hydrazone with an organometallic reagent to generate an alkenylmetal species, and reacting said alkenyllithium species with a $R^3$dialkylsilyl halide;
the organometallic reagent is butyllithium;
the alkenylmetal species is an alkenyllithium;
the $R^3$dialkylsilyl halide is BnMe$_2$SiCl;
in formula (I), $R^1$ is alkyl, $R^2$ is alkyl, $R^3$ is Ph-$CH_2$—, and $R^4$ is Ph-$CH_2$—;
in formula (I), $R^1$ is alkyl, $R^2$ is alkyl, $R^3$ is Ph-$CH_2$—, $R^4$ is Ph-$CH_2$—, and said $R^3$dialkylsilyl halide is BnMe$_2$SiCl; and
reacting said alkenyllithium species with a $R^3$dialkylsilyl halide comprises
reacting with from about 1.5 to about 2.0 equivalents of BnMe$_2$SiCl.

Additional embodiments of this invention are provided by processes that further comprise at least one of the following: transforming said compound of formula (I) into a salt; and transforming said compound of formula (I) into a hydrochloride salt.

Additional embodiments of this invention are provided by processes that further comprise at least one of the following:
cross-coupling the salt with an organo halide;
cross-coupling the salt with an organo halide that is an aryl iodide; and
cross-coupling the salt with an organo halide is an aryl bromide.

Additional embodiments of this invention are provided by compounds made by any one of the embodiments of the processes described herein and equivalents thereof.

Alkenylsilane Synthesis

Alkenylsilane reagent was synthesized by using the Shapiro reaction.[18] Illustrative embodiments of this strategy involved the conversion of an N-protected 4-piperidone into the corresponding tosylhydrazone, rearrangement to generate an alkenylmetal species, wherein the metal is for example Li, Na, K, or Mg, and finally trapping of this anionic intermediate with an $R^3$dialkylsilyl halide, such as an aryldialkylsilyl halide, for example benzyldimethylsilyl chloride (BnMe$_2$SiCl). Embodiments in which the metal in the alkenylmetal species is Mg are illustrated by alkenylmagnesium halides. In some embodiments of this invention, the alkenylmetal species is an alkenyllithium species. Other examples of $R^3$dialkylsilyl halide are provided by $R^3$dialkylsilyl halides wherein the halide is bromo or iodo. Embodiments of this invention included this synthetic route because it appeared to be the most direct. Other embodiments envisage the use of other common precursors to trisubstituted alkenes, such as alkynes or alkenyl halides. However, the use of these alternate precursors is envisaged to involve additional synthetic steps, as well as potential regioselectivity issues.

Some embodiments of this invention comprised a first conversion step to convert 1-benzyl-4-piperidone (1) into tosylhydrazone (2). Furthermore, embodiments of this invention used the benzyl protecting group because of its relatively high stability toward organometallic reagents like n-butyllithium.[19] Alkyllithium and alkylmagnesium halides are other examples of organometallic reagents. In some embodiments, tosylhydrazone formation was accomplished by adding (1) to p-toluenesulfonhydrazide in ethanol at ambient temperature, which led to the precipitation of (2) (Scheme 2). Tosylhydrazone (2) was isolated by filtration as a crystalline, white solid that was stable for at least 6 months on the bench top. This material was used without performing further purification.

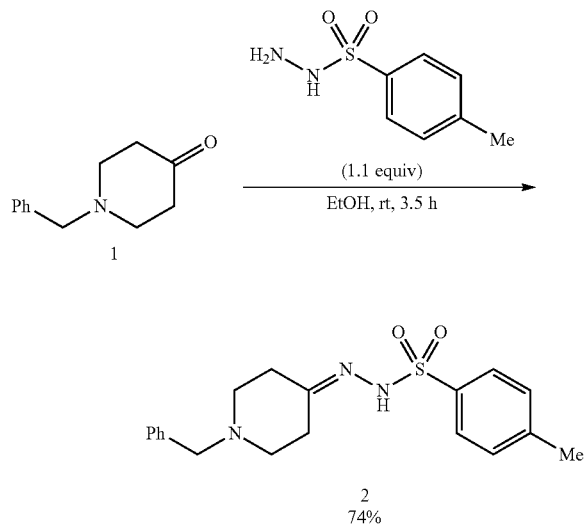

Scheme 2. Tosylhydrazone synthesis.

Embodiments of this invention comprised a second step that involved the Shapiro reaction of (2). Previous reports have shown that carbocyclic tosylhydrazones undergo the Shapiro reaction, followed by trapping with trimethylsilyl chloride (TMSCl), to generate cyclic, alkenyl trimethylsilanes.[20] These reference reactions employed a TMEDA/hexanes solvent system and used a large excess of both n-butyllithium (4.0-4.3 equiv) and TMSCl (3.4-4.0 equiv). Deprotonation of the tosylhydrazone was performed below −40° C., and subsequent rearrangement to the alkenyllithium intermediate occurred at ambient temperature over 1-3 hours. Some embodiments of this invention used these established reaction conditions as the starting point in the studies involving the Shapiro reaction of heterocyclic tosylhydrazone (2) and BnMe$_2$SiCl.

It was found in the studies performed in the context of this invention that the use of the literature conditions resulted in only a 60% isolated yield of desired alkenylsilane (4) (Scheme 3).

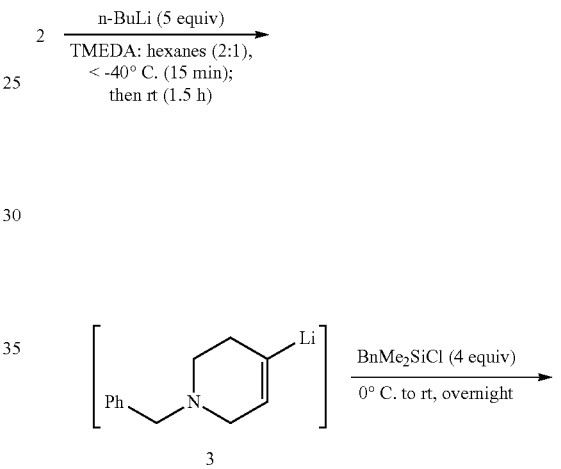

Scheme 3. Syntheis of alkenylsilane 4 using literature conditions.

It could be postulated in principle that embodiments that generated this low yield would implicate either incomplete consumption of tosylhydrazone (2) or premature protonation of alkenyllithium intermediate (3). In this regard, previous studies have suggested that unwanted protonation can occur via proton abstraction from the solvent, another hydrazone molecule, or the tosyl group.[18] The conversion of (2) and the ratio of the amounts of (5) and (6) (concisely "5:6") that formed were monitored by quenching reaction aliquots with deuterated methanol and analyzing them by HPLC and $^1$H NMR, respectively (Table 1).

TABLE 1

Shapiro reaction of 2: investigation of solvent and temperature.

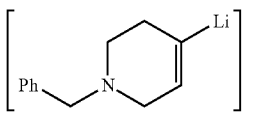

| entry[a] | solvent | equiv TMEDA | temp. | 30 min conv.[b] (5:6[c]) | 1 h conv.[b] (5:6[c]) | 1.5 h conv.[b] (5:6[c]) | 2 h conv.[b] (5:6[c]) | 3 h conv.[b] (5:6[c]) |
|---|---|---|---|---|---|---|---|---|
| 1 | TMEDA | 36 | rt | 86% (>20:1) | 93% (>20:1) | 96% (>20:1) | 97% (>20:1) | 97% (>20:1) |
| 2 | ether | 5 | rt | 81% (>20:1) | 91% (>20:1) | 93% (5:1) | 94% (4:1) | 95% (3:1) |
| 3 | MTBE | 5 | rt | 65% (>20:1) | 83% (6:1) | 87% (4:1) | 89% (3:1) | 92% (2:1) |
| 4 | toluene | 5 | rt | 68% (>20:1) | 80% (>20:1) | 85% (5:1) | 87% (3:1) | 90% (2:1) |
| 5 | THF | 5 | rt | 89% (2:1) | 98% (1:1) | >99% (1:3) | >99% (1:8) | — |
| 6 | THF | none | rt | 91% (6:1) | 96% (4:1) | 98% (2:1) | 99% (2:1) | — |
| 7 | THF | none | 0° C. | 51% (>20:1) | 66% (>20:1) | 80% (9:1) | 84% (4:1) | 91% (3:1) |

[a]0.2 M in solvent; 0.6 mmol scale.
[b]Calculated from 2:(5 + 6) ratio, which was determined by HPLC.
[c]Determined by $^1$H NMR.

This methodology tested in the context of this invention for both of the above-mentioned potential sources of yield loss. The results obtained in the context of this invention indicated that the reaction attained nearly quantitative conversion of (2) within about 1.5 hours, with negligible formation of (6) (entry 1). Over time, proton abstraction by (3) did not appear to be significant. Thus neither of the potential explanations that one would posit in light of reference teachings appeared to be responsible for the low yield shown in Scheme 3.

The use of alternate solvents in this reaction, including ether, methyl t-butyl ether (MTBE), toluene, and THF, was also investigated in the context of this invention. Embodiments that comprised the use of each of these solvents led to significant formation of (6) prior to complete consumption of (2) (entries 2-6). In THF, this unwanted protonation of (3) was slower at 0° C. than at ambient temperature (compare entries 6 and 7), but significant protonation still occurred at 0° C. before high conversion of (2) could be attained. Some embodiments of this invention use an aprotic solvent such that it is not subject to deprotonation even by strong bases.

Still other embodiments comprised reaction optimization by varying the equivalents of each reagent (Table 2). The initial reaction conditions comprised 5 equivalents of n-butyllithium, 33 equivalents of TMEDA, and 4 equivalents of BnMe$_2$SiCl (entry 1).

TABLE 2

Shapiro reaction of 2: investigation of reagent stoichiometries.

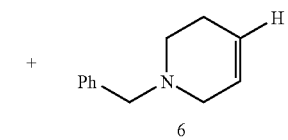

| entry[a] | X | Y | Z | isolated yield of 4 | isolated yield of 6 |
|---|---|---|---|---|---|
| 1 | 5 | 33 | 4 | 60% | 0% |
| 2 | 4 | 33 | 4 | 49% | 10-20%[b] |
| 3 | 3 | 33 | 4 | 5% | 47% |
| 4 | 5 | 5 | 4 | 65% | 0% |
| 5 | 5 | 5 | 2 | 83% | 0% |
| 6 | 5 | 5 | 1.5 | 81% | 0% |
| 7 | 5 | 5 | 1.1 | 62% | 10% |

[a]0.2 M; 26 mmol scale.
[b]Material contaminated with unknown impurities, preventing precise yield determination.

Compound (4) is an illustrative embodiment of compound of formula (I) wherein $R^3$ is benzyl (Bn). As appreciated by those of ordinary skill in the art, embodiments of this invention include other $R^3$ assignments. Such embodiments are obtained either from compound (4) by using known chemical reactions, or by using an aryldialkyl silyl halide that has another Si substituent group instead of benzyl and that can be used analogously as BnR¹R²SiCl is used in the illustrative embodiments of the Shapiro reaction described herein. Examples of such $R^3$ substituents include those provided in the definition of compounds of formula (I).

Embodiments of reagent BnR¹R²SiCl include reagents in which $R^1$ and $R^2$ are independently chosen to be $C_{1-4}$alkyl. The Z equivalents in Table 2 are given with reference to illustrative embodiments of this reagent when each of $R^1$ and $R^2$ is $CH_3$. Embodiments of this invention used, as suggested in the literature,[18,20-21] at least 5 equivalents of n-butyllithium to prevent protonation of (3) (compare entries 1-3). It was discovered in the context of this invention that TMEDA did not have to be used as a co-solvent. It was found in the context of this invention that the reaction could instead be carried out in hexanes with only 5 equivalents of TMEDA, resulting in a similar isolated yield of (4) (compare entries 1 and 4). It was also found in the context of this invention that the use of only 1.5-2 equivalents of BnR¹R²SiCl, for example BnMe₂SiCl, instead of 4 equivalents, significantly increased the isolated yield of (4) (compare entries 4-7). This finding is in clear contrast with reference literature teachings, which have suggested that roughly equal amounts of electrophile and n-butyllithium need to be employed.[18,20-21] Embodiments of this invention comprised this reaction successfully performed on scales of up to 52 mmol by using these optimized conditions found in the context of this invention. The use of tosylhydrazone (2) in embodiments of this invention is preferred to the use of the Boc-protected analog of tosylhydrazone (2) in light of the known instability of Boc-groups to n-butyllithium at temperatures greater than or at about 0° C.[19]

Embodiments of this invention that comprise the use of fewer equivalents of BnMe₂SiCl show that this invention leads to the increase of the yield of (4). In addition, embodiments of this invention that comprise the use of fewer equivalents of the aryldimethylsilyl halide, such as BnMe₂SiCl, show that the methodology developed in the context of this invention greatly facilitates the isolation of (4). The aqueous workups of the reactions shown in entries 1-4 of Table 2 comprised readily formed emulsions and large amounts of by-products interfering with the purification. In contrast, the workups of the reactions shown in entries 5-7 according to this invention did not generate emulsions and formed significantly fewer by-products, an advantageous feature of embodiments according to this invention. Although the methodology developed in the context of this invention is not limited by any specific theory or postulate, it is envisaged that the excess BnMe₂SiCl employed in entries 1-4 was the source of the cumbersome emulsions and by-products.

As those with ordinary skill in the art will appreciate on the basis of the disclosure provided herein, embodiments of this invention provide the synthesis of alkenylsilane (4). Features of this synthesis provide optimization features developed in the context of this invention. Furthermore, embodiments of this invention provide alkenylsilane (4) purification methodology. Silica gel chromatography was used to remove the majority of the impurities, but some minor silyl by-products remained. Because (4) existed as an oil, further direct purification was difficult to achieve in embodiments that comprised only the use of silica gel for purification. In other embodiments, alkenylsilane (4) was transformed into a salt. In some embodiments this salt is a pharmaceutically acceptable salt.

In still other embodiments, this salt was a hydrohalide salt. In further embodiments, this salt was the HCl salt (7) (Scheme 4). The salt was obtained by suitable reaction with the appropriate acid. In some embodiments, this was accomplished through reaction with 5N HCl. In other embodiments, this is accomplished in a nonaqueous environment, such as an HCl/ether solution, an HCl/dioxane solution, and chemically compatible mixtures thereof. Salt (7) was isolated by filtration in 85% yield as an amorphous, orange solid. Analytically pure (7) was obtained via recrystallization from acetonitrile, which generated a crystalline, white solid. Recrystallization is performed in other embodiments from other media such as isopropanol, hexane, THF, MTBE, diethylether, and chemically compatible mixtures thereof. Compound (7) was stable for at least 6 months on the bench top.

Scheme 4. Formation of HCl salt 7.

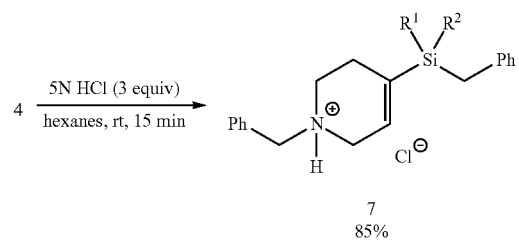

Palladium-Catalyzed Cross-Couplings Reactions

The applicability of alkenylsilane reagent (7) to palladium-catalyzed cross-coupling chemistry was also investigated in the context of this invention. Some previously reported reaction conditions for the cross-coupling of benzyldimethylsilanes[16] were employed. As shown in Table 3, compound (7) efficiently coupled with a variety of organo halides, such as aryl iodides. Other examples of such organo halides are provided by organo halides where the halide is one of Cl, Br and I. Other examples of such organo halides are provided by organo halides where the organo moiety is an unsaturated moiety, such as heteroaryl, alkyno, and alkyl. Embodiments of this invention comprised conditions different from those provided in reference literature procedures. In this regard, embodiments of this invention comprised the use of 4 equivalents of TBAF instead of 2 equivalents. It is envisaged that embodiments with this amount of TBAF provide for the conditions for the neutralization of (7). Furthermore, embodiments of this invention comprised the use of reaction times of more than 12 hours. It is believed that reaction times of about 12 h in embodiments of this invention are due to the basic amine that is present in (7) (after neutralization), and the possibility that it could coordinate to palladium.

Free base (4) also efficiently underwent cross-coupling reactions in other embodiments of this invention with organo halides, such as aryl iodides, under similar conditions (except with only 2 equivalents of TBAF). For example, the reaction of (4) with iodobenzene resulted in an 89% isolated yield of the cross-coupled product. However, because compound (7) could more easily be obtained in pure form, it was used to evaluate the full substrate scope of this reaction.

TABLE 3

Cross-coupling of 7 with aryl iodides.[a]

Reaction: 7 + I—R (1.5 equiv), TBAF (4 equiv), Pd₂dba₃—CHCl₃ (2 mol %), THF, 18-20 h → N-benzyl-4-R-tetrahydropyridine

| entry | I—R | temp. | isolated yield |
|---|---|---|---|
| 1 | I—C₆H₅ | rt | 90% |
| 2 | I—C₆H₄—Me (para) | rt | 91% |
| 3 | I—C₆H₄—Me (ortho) | rt | 62% |
| 4 | I—C₆H₄—Me (ortho) | 50° C. | 91% |
| 5 | I—C₆H₄—OMe (para) | rt | 88% |
| 6 | I—C₆H₄—OMe (ortho) | rt | 36% |
| 7 | I—C₆H₄—OMe (ortho) | 50° C. | 75% |
| 8 | 2-iodothiophene | rt | 64% |
| 9 | 2-iodothiophene | 50° C. | 60% |
| 10 | 3-iodothiophene | rt | 83% |
| 11 | I—C₆H₄—F | rt | 92% |
| 12 | I—C₆H₄—CF₃ | rt | 99% |
| 13 | I—C₆H₄—C(O)Me | rt | 99% |
| 14 | I—C₆H₄—C(O)OMe | rt | 93% |
| 15 | I—C₆H₄—CN | rt | 90% |
| 16 | I—C₆H₄—Br | rt | 65%[b] |
| 17 | I—C₆H₄—Br | 50° C. | 61%[b] |

[a] 0.2 M in THF; 0.3 mmol scale.
[b] None of the bromo-coupled product was isolated.

As to reaction yields, the trends that we observed matched those previously observed in alkenylsilane cross-coupling reactions.[15-16] Thus, electron-rich substrates (Table 3, entries 5-10) generally exhibited lower yields than electron-deficient ones (entries 11-15), and ortho-substituted substrates (entries 3 and 6) exhibited lower yields than para-substituted ones (entries 2 and 5). In some embodiments, reactions that gave isolated yields below 80% were further performed at a higher temperature of about 50° C. Increased temperature led to significantly higher yields in some embodiments (entries 4 and 7) but did not have a notable effect in others (entries 9 and 17). It was also found in the context of this invention that reaction with an iodo substituent was completely selective over reaction with a bromo substituent under these conditions (entries 16-17).

TABLE 4

Cross-coupling of 7 with aryl bromides.[a]

Reaction: 7 + Br—R (1.5 equiv), TBAF (4 equiv), THF, 18-20 h → N-benzyl-4-R-tetrahydropyridine

| entry | Br—R | catalyst/ligand | temp. | isolated yield |
|---|---|---|---|---|
| 1 | Br—C₆H₅ | Pd₂dba₃—CHCl₃ | rt | 0% |
| 2 | Br—C₆H₅ | Pd₂dba₃—CHCl₃ | 50° C. | 26% |
| 3 | Br—C₆H₅ | Pd₂dba₃—CHCl₃ | 90° C. | 42% |
| 4 | Br—C₆H₅ | PdBr₂/2-(t-Bu₂P)biphenyl | 50° C. | 74% |
| 5 | Br—C₆H₄—CF₃ | Pd₂dba₃—CHCl₃ | rt | 21% |
| 6 | Br—C₆H₄—CF₃ | Pd₂dba₃—CHCl₃ | 50° C. | 64% |
| 7 | Br—C₆H₄—CF₃ | Pd₂dba₃—CHCl₃ | 90° C. | 74% |
| 8 | Br—C₆H₄—CF₃ | PdBr₂/2-(t-Bu₂P)biphenyl | 50° C. | 80% |
| 9 | Br—C₆H₄—Me | PdBr₂/2-(t-Bu₂P)biphenyl | 50° C. | 89% |
| 10 | Br—C₆H₄—OMe | PdBr₂/2-(t-Bu₂P)biphenyl | 50° C. | 78% |

TABLE 4-continued

Cross-coupling of 7 with aryl bromides.[a]

7 + Br—R (1.5 equiv), TBAF (4 equiv), THF, 18-20 h → Ph-CH2-N-piperidinyl-R

| entry | Br—R | catalyst/ligand | temp. | isolated yield |
|---|---|---|---|---|
| 11 | Br-thiophene (3-bromothiophene) | PdBr$_2$/2-(t-Bu$_2$P)biphenyl | 50° C. | 45% |
| 12 | Br-C$_6$H$_4$-F | PdBr$_2$/2-(t-Bu$_2$P)biphenyl | 50° C. | 69% |
| 13 | Br-C$_6$H$_4$-C(O)Me | PdBr$_2$/2-(t-Bu$_2$P)biphenyl | 50° C. | 99% |
| 14 | Br-C$_6$H$_4$-C(O)OMe | PdBr$_2$/2-(t-Bu$_2$P)biphenyl | 50° C. | 84% |
| 15 | Br-C$_6$H$_4$-CN | PdBr$_2$/2-(t-Bu$_2$P)biphenyl | 50° C. | 94% |

[a]0.2 in THF or 0.1 M in 1,4-dioxane/THF (for 90° C. reactions), 2 mol % Pd$_2$dba$_3$—CHCl$_3$, 5 mol % PdBr$_2$, 10 mol % 2-(t-Bu$_2$P)biphenyl; 0.3 mmol scale.

The cross-coupling of compound (7) with organo halides, such as aryl bromides, was also investigated (Table 4). Embodiments of aryl bromide reactions that comprised the reaction conditions that had been applied to the aryl iodide couplings led to low isolated yields (entries 1 and 5). In some embodiments, raising the temperature led to some yield improvement (entries 2-3), and in other embodiments, such as those of a highly electron-deficient substrate bearing a para trifluoromethyl group (entries 6-7), the yield was significantly increased by raising the temperature. Embodiments that included the application of a PdBr$_2$/2-(di-tert-butylphosphino)biphenyl catalyst/ligand system (previously reported to facilitate the cross-coupling of a vinylpolysiloxane reagent with aryl bromides[22]) produced greatly improved yields for these cross-couplings (entries 4 and 8). These reaction conditions facilitated the efficient cross-coupling of a variety of aryl bromides with compound (7) (entries 9-15). Both electron-rich substrates (entries 9-11) and electron-deficient substrates (entries 8 and 12-15) gave yields that were comparable to those observed with the corresponding aryl iodides, with the exception of the thiophene substrate (entry 11). Other embodiments of this invention comprised halides with other functional groups such as ketones, esters, and nitriles.

It was shown in the context of this invention that piperidine compound (7), which contains an aryldialkylalkenylsilane moiety, is readily synthesized from 1-aryl-4-piperidone via a Shapiro reaction. Illustrative embodiments of this synthetic methodology have been provided herein. Because aryldialkylsilanes can easily be carried through multiple synthetic steps, piperidenyl silanes such as compound (7) can be further manipulated prior to undergoing cross-coupling. For example, those with ordinary skill in the art will appreciate that once the Shapiro reaction is performed according to this invention, then the N-benzyl moiety can be modified or replaced according to standard chemical reaction methodologies, and variations that comprise any of such known methodologies to modify or replace the benzyl moiety are envisaged within the scope of the present invention. In this regard, for example, the N-benzyl group of compound (7) (in its free base form (4)) is selectively removed via reaction with 1-chloroethylchloroformate,[23] without affecting the alkenylsilane moiety, and the resultant secondary amine is subsequently linked to another molecule through the formation of a new C—N bond prior to the cross-coupling reaction. To illustrate this transformation, embodiments of this invention comprised the formation and cross-coupling reaction of Boc-protected alkenylsilane (8), starting from (4) (Scheme 5).

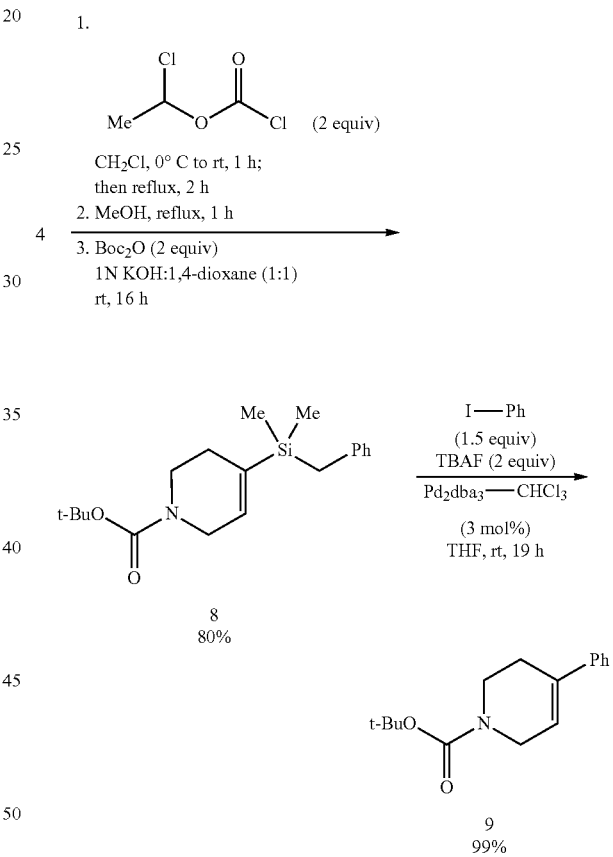

Scheme 5. Transformation of 4 into 8, following by cross-coupling of 8.

In contrast, such a transformation would be challenging with boronic acid or pinacol boronic ester reagents according to reference methodologies. Thus the chemistry demonstrated herein presents a useful method for 3,4-unsaturated piperidine synthesis that is not limited by the nature of specific N-substituents in the piperidine moiety. Because 3,4-unsaturated piperidines are one of the basic heterocyclic building blocks for drug candidates, the synthetic chemistry methodology of this invention provides new opportunities for drug discovery programs.

It was further shown in the context of this invention that piperidine compound (7) readily undergoes palladium-catalyzed cross-coupling reactions with a variety of aryl halides, such as iodides and bromides, to generate 3,4-unsaturated 4-arylpiperidines. Those with ordinary skill in the art will appreciate that the specific illustrative examples of halides given herein arte not limitations to the methodologies of this invention, but examples of their implementation, and that cross-coupling reactions with other halides that provide other chemically compatible moieties are envisaged within the scope of the present invention.

Embodiments of this invention also illustrate that a basic tertiary amine, such as compound (7) undergoes efficient cross-coupling. In contrast, reference methodologies teach that piperidine-derived coupling reagents usually possess non-basic, carbamate- or amide-protected amines.[1-2,5-7,13b-e,14] Furthermore, advantageous features of some embodiments of this invention include ambient reaction temperature conditions.

Other advantageous features of some embodiments of this invention include the low toxicity and high stability of silyl compound (7). This is in contrast with reference methodologies that teach tin and/or boron reagent-based processes.

Those with ordinary skill in the art will appreciate that the 3,4-unsaturated piperidines synthesized according to the methodologies of this invention can further be transformed according to known chemical processes. These further transformations include the substitution in the piperidine ring with chemically compatible substituent groups and the saturation of the 3,4-unsaturated piperidine ring. These further transformations coupled to the synthetic methodologies provided herein are envisaged within the scope of the present invention.

EXAMPLES

Compound (2): N-(1-Benzyl-piperidin-4-ylidene)-N'-tosyl-hydrazine

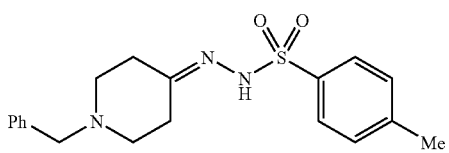

Even though this compound is available commercially, it was synthesized in embodiments of this invention. To a 2-L round-bottomed flask, under a nitrogen atmosphere, added 86 g (462 mmol) p-toluene sulfonhydrazide (1) and 1 L ethanol. With mechanical stirring, added 75 mL (420 mmol) 1-benzyl-4-piperidone. Let stir at room temperature for a total of 3.5 hours, then collected the precipitate via filtration, rinsing the filter cake with cold ethanol. Let the filter cake dry under vacuum (rt, ca. 0.2 torr) for a few hours, then ground the solid into a fine powder and placed under vacuum overnight (room temperature, ca. 200 millibarr). There was obtained 111 g of 2 as a crystalline, white solid (>95% purity by $^1$H NMR). This material was used in subsequent reactions. $^1$H NMR (500 MHz, CDCl$_3$): δ=7.82 (2H, d, J=8.3 Hz), 7.27 (5H, m), 3.49 (2H, s), 2.51 (2H, t, J=5.9 Hz), 2.46 (2H, t, J=6.0 Hz), 2.42 (3H, s), 2.34 (4H, m). $^{13}$C NMR (MHz, CDCl$_3$): δ=159.61, 143.93, 138.04, 135.37, 129.50, 128.89, 128.28, 128.06, 127.19, 62.26, 53.25, 51.84, 34.47, 26.83, 21.58. HRMS: M+H calculated for $C_{19}H_{23}N_3O_2S$=358.1584; observed m/z=358.1595 (−3.1 ppm).

Compound (4): 1-Benzyl-4-(benzyldimethylsilanyl)-1,2,3,6-tetrahydro-pyridine

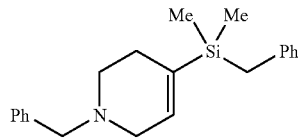

To a 1-L round-bottomed flask, added 18.6 g (52 mmol) 2 and 260 mL hexanes. Placed under a nitrogen atmosphere, added 40 mL (267 mmol) TMEDA, placed in a dry ice/acetone bath, and let stir for about 25 minutes. Via addition funnel, added 160 mL (256 mmol) n-butyllithium solution (1.6M in hexanes) dropwise over about 20 minutes. Let stir at −78° C. for 15 minutes after all of the n-butyllithium solution had been added, then removed flask from the dry ice bath and let stir for an additional 1.5 hours. Next, placed reaction in an ice bath, let stir for about 10 minutes, then added 14 mL (77 mmol) benzyldimethylsilyl chloride (neat) via syringe over about 1 minute. Let reaction stir overnight (ca. 16 hours), without maintaining the ice bath. The following day, placed reaction in an ice bath, let stir for about 15 minutes, and then slowly added 400 mL water, portionwise at first. Transferred to a separatory funnel, separated the aqueous and organic layers, and extracted the aqueous layer two times with 300 mL hexanes. Dried the combined organic layers with Na$_2$SO$_4$, concentrated in vacuo, and purified the crude material by silica gel chromatography (automated column, 330 g SiO$_2$, 0% to 20% EtOAc in hexanes gradient). Obtained 12.19 g of (4) as an orange oil (73%). $^1$H NMR (500 MHz, CDCl$_3$): δ=7.32 (5H, m), 7.21 (2H, t, J=7.6 Hz), 7.08 (1H, t, J=7.4 Hz), 7.00 (2H, d, J=7.0 Hz), 5.93 (1H, m), 3.59 (2H, s), 3.03 (2H, m), 2.53 (2H, t, J=5.6 Hz), 2.15 (2H, m), 2.15 (2H, s), 0.036 (6H, s). $^{13}$C NMR (100 MHz, CDCl$_3$): δ=140.09, 138.24, 135.16, 134.83, 129.16, 128.18, 128.17, 128.04, 126.97, 123.90, 62.98, 54.26, 49.72, 28.01, 25.05, −4.47. HRMS: M+H calculated for $C_{21}H_{27}NSi$=322.1986; observed m/z=322.2000 (−4.5 ppm).

Compound (7) with R$^1$ and R$^2$ being Me: 1-Benzyl-4-(benzyldimethylsilanyl)-1,2,3,6-tetrahydro-pyridine hydrochloride

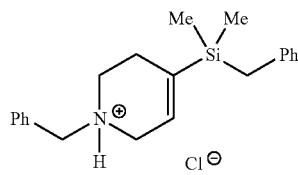

To a 250-mL round-bottomed flask, added 12.19 g (37.9 mmol) 4 and 76 mL hexanes. Let stir at room temperature for about 5 minutes, then added 11 mL (55 mmol) 5N HCl. Let stir at room temperature for 15 minutes, then collected the precipitate via filtration, rinsing the filter cake with approximately 50 mL cold hexanes. The filter cake was dried in a vacuum oven overnight (50° C., ca. 76 torr) to obtain 4.25 g of 7 as an orange solid. An additional 3.29 g of 7 precipitated from the mother liquor upon sitting at room temperature overnight. This material was collected and dried in a similar fashion. To the remaining mother liquor was added an additional 11 mL (55 mmol) 5N HCl. After stirring for 15 minutes at room temperature, the precipitate was collected and dried as before to generate another 4.05 g of 7. All batches of 7 were combined to obtain a total of 11.59 g of 7 as an orange, amorphous solid. The total isolated yield of 7 was 85%. Analytically pure 7 was obtained via recrystallization by adding 5 g (14 mmol) of crude 7 to 30 mL acetonitrile, heating in a 90° C. oil bath (with stirring) until all of 7 had dissolved, and finally letting the solution slowing cool to <30° C. (with stirring). A precipitate was generated during the cooling period, which was collected by filtration, rinsing the filter cake with approximately 40 mL cold acetonitrile. The filter cake was dried overnight in a vacuum oven (50° C., ca. 127 torr) to obtain 2.63 g of 7 as a crystalline, white solid (53%). $^1$H NMR (500 MHz, CDCl$_3$): δ=12.61 (1H, s), 7.63 (2H, m), 7.40 (3H, m), 7.18 (2H, t, J=7.6 Hz), 7.05 (1H, t, J=7.4 Hz), 6.96 (2H, d, J=7.1 Hz), 5.75 (1H, m), 4.18 (1H, dd, J=13.0, 5.4 Hz), 4.08 (1H, dd, J=13.0, 5.8 Hz), 3.74 (1H, d, J=17.0 Hz), 3.32 (2H, m), 2.84 (1H, m), 2.68 (1H, m), 2.14 (2H, s), 2.12 (1H, m), 0.085 (3H, s), 0.080 (3H, s). $^{13}$C NMR (125 MHz, CDCl$_3$): δ=138.98, 137.38, 131.16, 129.96, 129.21, 128.37, 128.29, 128.00, 126.83, 124.36, 58.24, 49.23, 47.25, 24.77, 23.19, −4.50, −4.54. HRMS: M+H calculated for C$_{21}$H$_{28}$NSi=323.2064; observed m/z=323.2079 (−4.7 ppm). Elemental analysis: calculated: C, 70.46%, H, 7.88%, N, 3.91%; observed: C, 70.71% (−0.25%); H, 8.17% (−0.29%); N, 4.01% (−0.10%). Melting point=173-175° C.

Compound (8) with R$^1$ and R$^2$ being Me: 4-(Benzyldimethylsilanyl)-3,6-dihydro-2H-pyridine-1-t-butoxycarbonyl

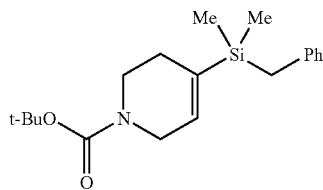

To a 250-mL round-bottomed flask, added 7.2 g (16.8 mmol) (4) and 170 mL CH$_2$Cl$_2$. Placed, under a nitrogen atmosphere, in an ice bath. When the internal temperature fell below 4° C., added 2.8 mL (25.7 mmol) 1-chloroethylchloroformate. Let temperature rise gradually to 18° C. over about 2 hours, then heated to reflux via heating mantle. Let stir at reflux for 2 hours. Next, let cool to room temperature, removed solvent in vacuo, added 170 mL MeOH, and then let stir at reflux for 1 hour. After letting cool to room temperature, added 85 mL 1,4-dioxane, 85 mL 1N aqueous KOH solution, and 5.5 g (25.2 mmol) di-t-butyl dicarbonate. Let stir at room temperature overnight. Extracted 3 times with 250 mL methyl t-butyl ether, dried with Na$_2$SO$_4$, and purified by silica gel chromatography (automated column, 120 g SiO$_2$, 0% to 10% EtOAc in hexanes gradient). Partitioned column fractions into 2 parts: first part contained 3.0 g of a yellow oil, which was shown to be (8) (ca. 90% purity by $^1$H NMR); second part contained 1.8 g of a yellow oil that became a solid upon refrigeration, which was shown to be 8 (>95% purity by $^1$H NMR). Overall yield was approximately 80%. $^1$H NMR (600 MHz, DMSO-d$_6$, 80° C.): δ=7.18 (2H, t, J=7.5 Hz), 7.04 (1H, t, J=7.3 Hz), 6.99 (2H, d, J=7.6 Hz), 5.92 (1H, s), 3.83 (2H, m), 3.34 (2H, t, J=5.6 Hz), 2.15 (2H, s), 2.05 (2H, br), 1.43 (9H, s), 0.030 (6H, s). $^{13}$C NMR (150 MHz, DMSO-d$_6$, 80° C.): δ=153.48, 139.08, 134.94, 133.21, 127.43, 127.35, 123.33, 78.07, 43.86, 39.53, 27.63, 26.05, 23.79, −4.96. HRMS: M+H calculated for C$_{19}$H$_{29}$NO$_2$Si=332.2040; observed m/z=332.2036 (−1.3 ppm). Applied the more pure portion of (8) to the cross-coupling reaction, generating compound (9).[14b]

Illustrative Cross-Coupling Procedure

To a 4-mL vial, added 100 mg (0.28 mmol) (7) and 6 mg (0.0058 mmol) Pd$_2$dba$_3$-CHCl$_3$. Next added 0.3 mL THF, 48 μL (0.43 mmol) iodobenzene, and finally 1.1 mL (1.1 mmol) TBAF solution (1M in THF). Let stir at room temperature for 18 hours. At the end of the reaction, added 200 μL triethylamine, let stir briefly, concentrated in vacuo, and purified the crude material directly by silica gel chromatography (automated column, 12 g SiO$_2$, 0% to 20% EtOAc in hexanes gradient). Obtained 63 mg (90%) of 1-Benzyl-4-phenyl-1,2,3,6-tetrahydro-pyridine as a yellow oil.

1-Benzyl-4-phenyl-1,2,3,6-tetrahydro-pyridine

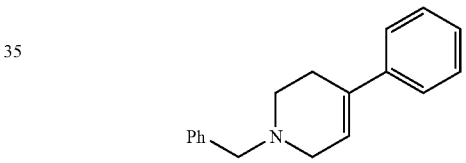

$^1$H NMR (400 MHz, CDCl$_3$): δ=7.30 (10H, m), 6.05 (1H, m), 3.63 (2H, s), 3.17 (2H, m), 2.71 (2H, t, J=5.7 Hz), 2.56 (2H, m). $^{13}$C NMR (125 MHz, CDCl$_3$): δ=140.87, 138.20, 134.93, 129.20, 128.23, 128.21, 127.07, 126.89, 124.86, 121.87, 62.70, 53.28, 49.93, 27.99. HRMS: M+H calculated for C$_{18}$H$_{19}$N=250.1590; observed m/z=250.1602 (−4.7 ppm).

1-Benzyl-4-p-tolyl-1,2,3,6-tetrahydro-pyridine

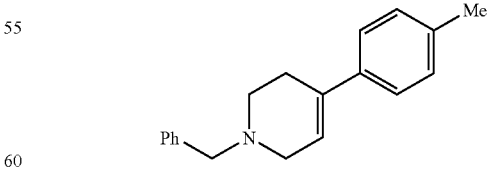

$^1$H NMR (500 MHz, CDCl$_3$): δ=7.33 (7H, m), 7.11 (2H, d, J=7.9 Hz), 6.02 (1H, m), 3.63 (2H, s), 3.16 (2H, m), 2.70 (2H, t, J=5.7 Hz), 2.54 (2H, m), 2.32 (3H, s). $^{13}$C NMR (125 MHz, CDCl$_3$): δ=138.26, 138.04, 136.52, 134.73, 129.19, 128.90, 128.21, 127.04, 124.73, 121.01, 62.73, 53.31, 49.96, 28.02, 21.01. HRMS: M+H calculated for $C_{19}H_{21}N$=264.1747; observed m/z=264.1741 (2.2 ppm).

1-Benzyl-4-o-tolyl-1,2,3,6-tetrahydro-pyridine

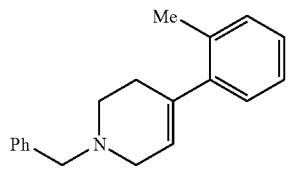

$^1$H NMR (500 MHz, CDCl$_3$): δ=7.37 (2H, d, J=8.3 Hz), 7.32 (2H, t, J=7.4 Hz), 7.25 (1H, t, J=7.2 Hz), 7.11 (4H, m), 5.51 (1H, m), 3.64 (2H, s), 3.13 (2H, m), 2.67 (2H, t, J=5.6 Hz), 2.35 (2H, m), 2.28 (3H, s). $^{13}$C NMR (125 MHz, CDCl$_3$): δ=142.90, 138.18, 137.03, 134.95, 130.03, 129.18, 128.19, 127.02, 126.67, 125.51, 123.63, 62.69, 52.86, 49.83, 30.74, 19.88. HRMS: M+H calculated for $C_{19}H_{21}N$=264.1747; observed m/z=264.1746 (0.3 ppm).

1-Benzyl-4-(4-methoxy-phenyl)-1,2,3,6-tetrahydro-pyridine

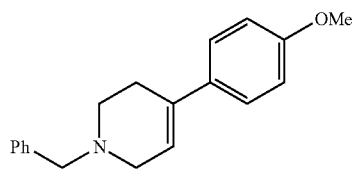

$^1$H NMR (500 MHz, CDCl$_3$): δ=7.30 (7H, m), 6.83 (2H, d, J=8.9 Hz), 5.96 (1H, m), 3.78 (3H, s), 3.62 (2H, s), 3.15 (2H, m), 2.69 (2H, t, J=5.7 Hz), 2.52 (2H, m). $^{13}$C NMR (125 MHz, CDCl$_3$): δ=158.65, 138.27, 134.24, 133.49, 129.17, 128.20, 127.02, 125.88, 120.18, 113.56, 62.72, 55.18, 53.30, 49.97, 28.06. HRMS: M+H calculated for $C_{19}H_{21}NO$=280.1696; observed m/z=280.1702 (−2.2 ppm).

1-Benzyl-4-(2-methoxy-phenyl)-1,2,3,6-tetrahydro-pyridine

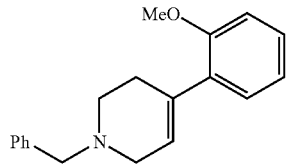

$^1$H NMR (500 MHz, CDCl$_3$): δ=7.40 (2H, d, J=7.1 Hz), 7.34 (2H, t, J=7.5 Hz), 7.22 (3H, m), 6.91 (1H, td, J=7.5, 0.77 Hz), 6.86 (1H, d, J=8.2 Hz), 5.79 (1H, m), 3.80 (3H, s), 3.66 (2H, s), 3.18 (2H, m), 2.69 (2H, t, J=5.7 Hz), 2.56 (2H, m). $^{13}$C NMR (125 MHz, CDCl$_3$): δ=156.78, 138.25, 135.50, 131.85, 129.35, 129.25, 128.16, 128.01, 126.98, 123.92, 120.50, 110.72, 62.78, 55.29, 53.21, 49.87, 29.45. HRMS: M+H calculated for $C_{19}H_{21}NO$=280.1696; observed m/z=280.1697 (−0.4 ppm).

1-Benzyl-4-thiophen-2-yl-1,2,3,6-tetrahydro-pyridine

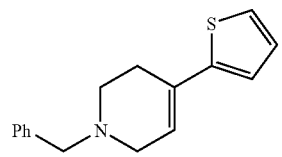

$^1$H NMR (400 MHz, CDCl$_3$): δ=7.32 (5H, m), 7.10 (1H, dd, J=4.8, 1.6 Hz), 6.94 (2H, m), 6.07 (1H, m), 3.62 (2H, s), 3.14 (2H, m), 2.69 (2H, t, J=5.7 Hz), 2.56 (2H, m). $^{13}$C NMR (125 MHz, CDCl$_3$): δ=145.42, 138.20, 129.65, 129.10, 128.24, 127.12, 127.08, 123.13, 121.67, 120.99, 62.53, 52.87, 49.59, 28.30. HRMS: M+H calculated for $C_{16}H_{17}NS$=256.1154; observed m/z=256.1160 (−2.2 ppm).

1-Benzyl-4-thiophen-3-yl-1,2,3,6-tetrahydro-pyridine

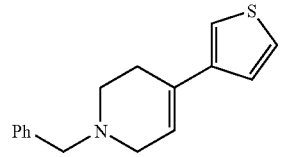

$^1$H NMR (500 MHz, CDCl$_3$): δ=7.28 (7H, m), 7.06 (1H, m), 6.04 (1H, m), 3.61 (2H, s), 3.13 (2H, m), 2.68 (2H, t, J=5.7 Hz), 2.52 (2H, m). $^{13}$C NMR (125 MHz, CDCl$_3$): δ=142.6, 138.29, 130.44, 129.13, 128.22, 127.05, 125.33, 124.62, 121.01, 118.56, 62.65, 52.96, 49.75, 28.05. HRMS: M+H calculated for $C_{16}H_{17}NS$=256.1154; observed m/z=256.1163 (−3.3 ppm).

1-Benzyl-4-(4-fluoro-phenyl)-1,2,3,6-tetrahydro-pyridine

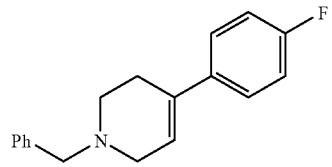

$^1$H NMR (400 MHz, CDCl$_3$): δ=7.32 (7H, m), 6.98 (2H, t, J=8.8 Hz), 5.99 (1H, m), 3.63 (2H, s), 3.15 (2H, m), 2.70 (2H, t, J=5.7 Hz), 2.52 (2H, m). $^{13}$C NMR (125 MHz, CDCl$_3$): δ=161.96 (d, J=246 Hz), 138.15, 136.95 (d, J=3.2 Hz), 134.01, 129.18, 128.25, 127.11, 126.37 (d, J=7.8 Hz), 121.77, 114.99 (J=21 Hz). HRMS: M+H calculated for $C_{18}H_{18}NF$=268.1496; observed m/z=268.1506 (−3.7 ppm).

1-Benzyl-4-(4-trifluoromethyl-phenyl)-1,2,3,6-tetrahydro-pyridine

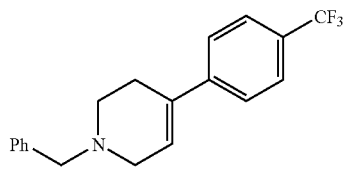

$^{1}$H NMR (400 MHz, CDCl$_3$): δ=7.50 (2H, d, J=8.3 Hz), 7.40 (2H, d, J=8.2 Hz), 7.29 (5H, m), 6.09 (1H, m), 3.59 (2H, s), 3.13 (2H, m), 2.66 (2H, t, J=5.7 Hz), 2.49 (2H, m). $^{13}$C NMR (100 MHz, CDCl$_3$): δ=144.17, 138.02, 133.83, 129.07, 128.71 (q, J=32 Hz), 128.21, 127.08, 125.10 (q, J=3.8 Hz), 124.95, 124.25 (q, J=272 Hz), 124.14, 62.56, 53.13, 49.63, 27.83. HRMS: M+H calculated for $C_{19}H_{18}NF_3$=318.1464; observed m/z=318.1468 (−1.2 ppm).

1-[4-(1-Benzyl-1,2,3,6-tetrahydro-pyridin-4-yl)-phenyl]-ethanone

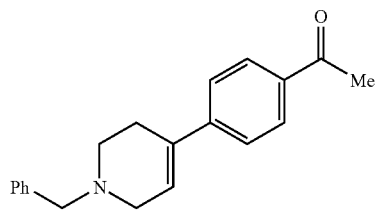

$^{1}$H NMR (400 MHz, CDCl$_3$): δ=7.88 (2H, d, J=8.6 Hz), 7.44 (2H, d, J=8.5 Hz), 7.30 (5H, m), 6.19 (1H, m), 3.62 (2H, s), 3.17 (2H, m), 2.71 (2H, t, J=5.7 Hz), 2.56 (2H, m), 2.55 (3H, s). $^{13}$C NMR (125 MHz, CDCl$_3$): δ=197.50, 145.28, 138.03, 135.50, 134.10, 129.08, 128.41, 128.22, 127.08, 124.76, 124.46, 62.58, 53.25, 49.70, 27.78, 26.44. HRMS: M+H calculated for $C_{20}H_{21}NO$=292.1696; observed m/z=292.1707 (−3.8 ppm).

4-(1-Benzyl-1,2,3,6-tetrahydro-pyridin-4-yl)-benzoic acid methyl ester

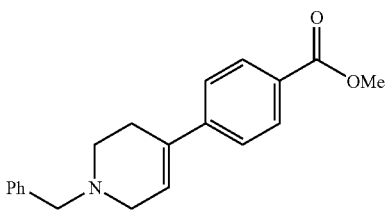

$^{1}$H NMR (500 MHz, CDCl$_3$): δ=7.97 (2H, d, J=8.5 Hz), 7.43 (2H, d, J=8.5 Hz), 7.34 (5H, m), 6.19 (1H, m), 3.89 (3H, s), 3.63 (2H, s), 3.18 (2H, m), 2.71 (2H, t, J=5.7 Hz), 2.56 (2H, m). $^{13}$C NMR (125 MHz, CDCl$_3$): δ=166.89, 145.14, 138.08, 134.17, 129.58, 129.09, 128.41, 128.23, 127.09, 124.61, 124.24, 62.60, 53.25, 51.91, 49.74, 27.81. HRMS: M+H calculated for $C_{20}H_{21}NO_2$=308.1645; observed m/z=308.1647 (−0.6 ppm).

4-(1-Benzyl-1,2,3,6-tetrahydro-pyridin-4-yl)-benzonitrile

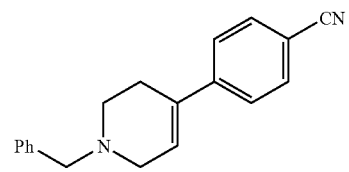

$^{1}$H NMR (500 MHz, CDCl$_3$): δ=7.58 (2H, d, J=8.6 Hz), 7.45 (2H, d, J=8.5 Hz), 7.32 (5H, m), 6.20 (1H, m), 3.64 (2H, s), 3.19 (2H, m), 2.72 (2H, t, J=5.7 Hz), 2.53 (2H, m). $^{13}$C NMR (125 MHz, CDCl$_3$): δ=145.08, 137.92, 133.62, 132.06, 129.07, 128.25, 127.13, 125.40, 125.28, 118.95, 110.21, 62.53, 53.17, 49.58, 27.66. HRMS: M+H calculated for $C_{19}H_{18}N_2$=275.1543; observed m/z=275.1554 (−4.1 ppm).

1-Benzyl-4-(4-bromo-phenyl)-1,2,3,6-tetrahydro-pyridine

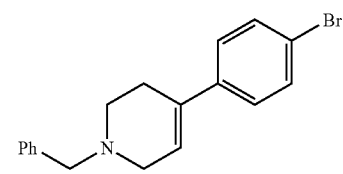

$^{1}$H NMR (400 MHz, CDCl$_3$): δ=7.32 (9H, m), 6.05 (1H, m), 3.63 (2H, s), 3.14 (2H, m), 2.70 (2H, t, J=5.7 Hz), 2.50 (2H, m). $^{13}$C NMR (125 MHz, CDCl$_3$): δ=139.73, 138.14, 133.96, 131.29, 129.16, 128.26, 127.11, 126.48, 122.59, 120.72, 62.67, 53.24, 49.80, 27.91. HRMS: M+H calculated for $C_{18}H_{18}NBr$=328.0695; observed m/z=328.0702 (−2.0 ppm).

REFERENCES

1. Levell, J.; Astles, P.; Eastwood, P.; Cairns, J.; Houille, O.; Aldous, S.; Merriman, G.; Whiteley, B.; Pribish, J.; Czekaj, M.; Liang, G.; Maignan, S.; Guilloteau, J-. P.; Dupuy, A.; Davidson, J.; Harrison, T.; Morley, A.; Watson, S.; Fenton, G.; McCarthy, C.; Romano, J.; Mathew, R.; Engers, D.; Gardyan, M.; Sides, K.; Kwong, J.; Tsay, J.; Rebello, S.; Shen, L.; Wang, J.; Luo, Y.; Giardino, O.; Lim, H-. K.; Smith, K.; Pauls, H. *Bioorg. Med. Chem.* 2005, 13, 2859-2872.
2. Cody, W. L.; Holsworth, D. D.; Powell, N. A.; Jalaie, M.; Zhang, E.; Wang, W.; Samas, B.; Bryant, J.; Ostroski, R.; Ryan, M. J.; Edmunds, J. J. *Bioorg. Med. Chem.* 2005, 13, 59-68.
3. (a) Mewshaw, R. E.; Meagher, K. L.; Zhou, P.; Zhou, D.; Shi, X.; Scerni, R.; Smith, D.; Schechter, L. E.; Andree, T. H. *Bioorg. Med. Chem. Lett.* 2002, 12, 307-310. (b) Saari, W. S.; Halczenko, W.; Huff, J. R.; Guare, Jr., J. P.; Hunt, C. A.; Randall, W. C.; Lotti, V. J.; Yarbrough, G. G. *J. Med.*

*Chem.* 1984, 27, 1182-1185. (c) Martin, L. L.; Klioze, S. S.; Worm, M.; Crichlow, C. A. *J. Med. Chem.* 1979, 22, 1347-1354.

4. (a) Filla, S. A.; Mathes, B. M.; Johnson, K. W.; Phebus, L. A.; Cohen, M. L.; Nelson, D. L.; Zgombick, J. M.; Erickson, J. A.; Schenck, K. W.; Wainscott, D. B.; Brancheck, T. A.; Schaus, J. M. *J. Med. Chem.* 2003, 46, 3060-3071. (b) Isaac, M.; Slassi, M.; Xin, T.; Arora, J.; O'Brien, A.; Edwards, L.; MacLean, N.; Wilson, J.; Demschyshyn, L.; Labrie, P.; Naismith, A.; Maddaford, S.; Papac, D.; Harrison, S.; Wang, H.; Draper, S.; Tehim, A. *Bioorg. Med. Chem. Lett.* 2003, 13, 4409-4413.

5. (a) Quesnelle, C. A.; Gill, P.; Roy, S.; Dodier, M.; Marinier, A.; Martel, A.; Snyder, L. B.; D'Andrea, S. V.; Bronson, J. J.; Frosco, M.; Beaulieu, D.; Warr, G. A.; DenBleyker, K. L.; Stickle, T. M.; Yang, H.; Chaniewski, S. E.; Ferraro, C. A.; Taylor, D.; Russell, J. W.; Santone, K. S.; Clarke, J.; Drain, R. L.; Knipe, J. O.; Mosure, K.; Barrett, J. F. *Bioorg. Med. Chem. Lett.* 2005, 15, 2728-2733. (b) Barbachyn, M. R.; Cleek, G. J.; Dolak, L. A.; Garmon, S. A.; Morris, J.; Seest, E. P.; Thomas, R. C.; Toops, D. S.; Watt, W.; Wishka, D. G.; Ford, C. W.; Zurenko, G. E.; Hamel, J. C.; Schaadt, R. D.; Stapert, D.; Yagi, B. H.; Adams, W. J.; Friis, J. M.; Slatter, J. G.; Sams, J. P.; Oien, N. L.; Zaya, M. J.; Wienkers, L. C.; Wynalda, M. A. *J. Med. Chem.* 2003, 46, 284-302.

6. Barrow, J. C.; Nantermet, P. G.; Selnick, H. G.; Glass, K. L.; Rittle, K. E.; Gilbert, K. F.; Steele, T. G.; Homnick, C. F.; Freidinger, R. M.; Ransom, R. W.; Kling, P.; Reiss, D.; Broten, T. P.; Schorn, T. W.; Chang, R. S. L.; O'Malley, S. S.; Olah, T. V.; Ellis, J. D.; Barrish, A.; Kassahun, K.; Leppert, P.; Nagarathnam, D.; Forray, C. *J. Med. Chem.* 2000, 43, 2703-2718.

7. Tan, Q.; Birzin, E. T.; Chan, W.; Yang, Y. T.; Pai, L.-. Y.; Hayes, E. C.; DaSilva, C. A.; DiNinno, F.; Rohrer, S. P.; Schaeffer, J. M.; Hammond, M. L. *Bioorg. Med. Chem. Lett.* 2004, 14, 3747-3751.

8. Wenzel, B.; Sorger, D.; Heinitz, K.; Scheunemann, M.; Schliebs, R.; Steinbach, J.; Sabri, O. *Eur. J. Med. Chem.* 2005, 40, 1197-1205.

9. Guzikowski, A. P.; Tamiz, A. P.; Acosta-Burruel, M.; Hong-Bae, S.; Cai, S. X.; Hawkinson, J. E.; Keana, J. F. W.; Kesten, S. R.; Shipp, C. T.; Tran, M.; Whittemore, E. R.; Woodward, R. M.; Wright, J. L.; Zhou, Z-. L. *J. Med. Chem.* 2000, 43, 984-994.

10. Sakamuri, S.; Enyedy, I. J.; Kozikowski, A. P.; Zaman, W. A.; Johnson, K. M.; Wang, S. *Bioorg. Med. Chem. Lett.* 2001, 11, 495-500.

11. Fonquerna, S.; Miralpeix, M.; Pagès, L.; Puig, C.; Cardús, A.; Antón, F.; Vilella, D.; Aparici, M.; Prieto, J.; Warrellow, G.; Beleta, J.; Ryder, H. *Bioorg. Med. Chem. Lett.* 2005, 15, 1165-1167.

12. (a) Shkavrov, S; Popov, S.; Kravchenko, D.; Krasavin, M. *Synth. Commun.* 2005, 35, 725-730. (b) Peterson, B. R.; Wallimann, P.; Carcanague, D. R.; Diederich, F. *Tetrahedron* 1995, 51, 401-421. (c) Barnett, C. J.; Copley-Merriman, C. R.; Maki, J. *J. Org. Chem.* 1989, 54, 4795-4800. (d) Zimmerman, D. M.; Cantrell, B. E.; Reel, J. K.; Hemrick-Luecke, S. K.; Fuller, R. W. *J. Med. Chem.* 1986, 29, 1517-1520.

13. (a) Bica, K.; Gaertner, P. *Org. Lett.* 2006, 8, 733-735. (b) Nakamura, M.; Ito, S.; Matsuo, K.; Nakamura, E. *Synlett* 2005, 11, 1794-1798. (c) Corley, E. G.; Conrad, K.; Murry, J. A.; Savarin, C.; Holko, J.; Boice, G. *J. Org. Chem.* 2004, 69, 5120-5123. (d) Powell, D. A.; Fu, G. C. *J. Am. Chem. Soc.* 2004, 126, 7788-7789. (e) Billotte, S. *Synlett* 1998, 4, 379-380.

14. (a) Larsen, U. S.; Martiny, L.; Begtrup, M. *Tetrahedron Lett.* 2005, 46, 4261-4263. (b) Scheiper, B.; Bonnekessel, M.; Krause, H.; Fürstner, A. *J. Org. Chem.* 2004, 69, 3943-3949. (c) Boice, G. N.; Savarin, C. G.; Murry, J. A.; Conrad, K.; Matty, L.; Corley, E. G.; Smitrovich, J. H.; Hughes, D. *Tetrahedron* 2004, 60, 11367-11374. (d) Dantale, S. W.; Söderberg, B. C. G. *Tetrahedron* 2003, 59, 5507-5514. (e) Bursavich, M. G.; West, C. W.; Rich, D. H. *Org. Lett.* 2001, 3, 2317-2320. (f) Eastwood, P. R. *Tetrahedron Lett.* 2000, 41, 3705-3708. (g) Kiely, J. S.; Laborde, E.; Lesheski, L. E.; Bucsh, R. A. *J. Heterocycl. Chem.* 1991, 28, 1581-1585. (h) Wustrow, D. J.; Wise, L. D. *Synthesis* 1991, 11, 993-995.

15. (a) Denmark, S. E.; Sweis, R. F. Organosilicon Compounds in Cross-Coupling Reactions. In *Metal-Catalyzed Cross-Coupling Reactions*, 2nd ed.; de Meijere, A.; Diederich, F., Eds.; Wiley-VCH: Weinheim, 2004; pp 163-216. (b) Denmark, S. E.; Sweis, R. F. *Acc. Chem. Res.* 2002, 35, 835-846. (c) Denmark, S. E.; Sweis, R. F. *Chem. Pharm. Bull.* 2002, 50, 1531-1541.

16. Trost, B. M.; Machacek, M. R.; Ball, Z. T. *Org. Lett.* 2003, 5, 1895-1898.

17. (a) Denmark, S. E.; Fujimori, S. *J. Am. Chem. Soc.* 2005, 127, 8971-8973. (b) Trost, B. M.; Frederiksen, M. U.; Papillon, J. P. N.; Harrington, P. E.; Shin, S.; Shireman, B. T. *J. Am. Chem. Soc.* 2005, 127, 3666-3667.

18. (a) Adlington, R. M.; Barrett, A. G. M. *Acc. Chem. Res.* 1983, 16, 55-59. (b) Chamberlin, A. R.; Bloom, S. H. Lithioalkenes from Arenesulfonylhydrazones. In *Organic Reactions*; Paquette, L. A., Ed.; John Wiley & Sons, Inc., 1990; Vol. 39, pp 1-83. (c) Shapiro, R. H. Alkenes from Tosylhydrazones. In *Organic Reactions*; Dauben, W. G., Ed.; John Wiley & Sons, Inc., 1976; Vol. 23, pp 405-507.

19. Greene, T. W.; Wuts, P. G. M. *Protective Groups in Organic Synthesis*, 2nd ed.; John Wiley & Sons, Inc., 1991; pp 441-452.

20. (a) Barth, W.; Paquette, L. A. *J. Org. Chem.* 1985, 50, 2438-2443. (b) Paquette, L. A.; Fristad, W. E.; Dime, D. S.; Bailey, T. R. *J. Org. Chem.* 1980, 45, 3017-3028.

21. Chamberlin, A. R.; Stemke, J. E.; Bond, F. T. *J. Org. Chem.* 1978, 43, 147-154.

22. Denmark, S. E.; Butler, C. R. *Org. Lett.* 2006, 8, 63-66.

23. Huttenloch, O.; Laxman, E.; Waldmann, H. *Chem. Eur. J.* 2002, 8, 4767-4780.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

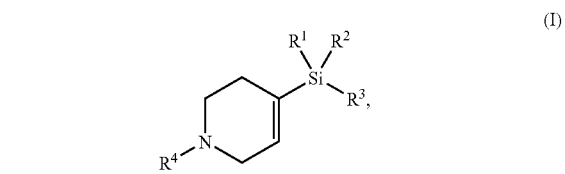

wherein $R^1$ and $R^2$ are independently chosen from the group of alkyl, and alkyl substituted with at least one of halo, hydroxy, alkoxy, —COOH, and —COOAlkyl;

$R^3$ is chosen from the group of H, Ar, heteroaryl, fluoro, hydroxyl, —$OR^1$, and —O—$R^5$;

$R^5$ is

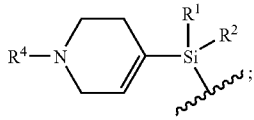

and $R^4$ is chosen from the group of Ar, cycloalkyl, heterocycloalkyl, and heteroaryl, where $R^3$ and $R^4$ are independently optionally substituted with at least one of halo, hydroxy, alkoxy, —COOH, and —COOAlkyl;

or a salt thereof.

2. A compound as in claim 1, wherein $R^4$ is Ph-$CH_2$—.

3. A compound as in claim 1, wherein $R^1$ is alkyl and $R^2$ is alkyl.

4. A compound as in claim 1, wherein $R^1$ is methyl and $R^2$ is methyl.

5. A compound as in claim 1, wherein $R^3$ is Ar.

6. A compound as in claim 1, wherein $R^3$ is Ph-$CH_2$—.

7. A compound as in claim 1, wherein $R^3$ is —O—$R^5$.

8. A compound as in claim 1, wherein $R^1$ is alkyl, $R^2$ is alkyl, $R^3$ is Ph-$CH_2$—, and $R^4$ is Ph-$CH_2$—.

9. A compound as in claim 1, wherein said salt is a hydrochloride salt.

10. A compound as in claim 8, wherein said salt is a hydrochloride salt.

11. A process for the preparation of an unsaturated piperidine, comprising making a compound of formula (I) from a hydrazone, and said compound of formula (I) is

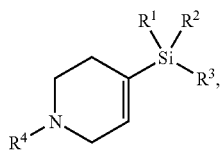 (I)

wherein $R^1$ and $R^2$ are independently chosen from the group of alkyl, and alkyl substituted with at least one of halo, hydroxy, alkoxy, —COOH, and —COOAlkyl;

$R^3$ is chosen from the group of H, Ar, heteroaryl, fluoro, hydroxyl, —$OR^1$, and —O—$R^5$;

$R^5$ is

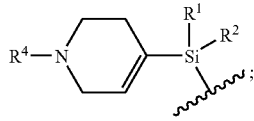

and $R^4$ is chosen from the group of Ar, cycloalkyl, heterocycloalkyl, and heteroaryl, where $R^3$ and $R^4$ are independently optionally substituted with at least one of halo, hydroxy, alkoxy, —COOH, and —COOAlkyl;

and salts thereof.

12. A process as in claim 11, wherein said compound of formula (I) is obtained by reacting a hydrazone with an organometallic reagent to generate an alkenylmetal species, and reacting said alkenyllithium species with a $R^3$dialkylsilyl halide.

13. A process as in claim 12, wherein said organometallic reagent is butyllithium.

14. A process as in claim 12, wherein said alkenylmetal species is an alkenyllithium.

15. A process as in claim 12, wherein said $R^3$dialkylsilyl halide is $BnMe_2SiCl$.

16. A process as in claim 12, wherein $R^1$ is alkyl, $R^2$ is alkyl, $R^3$ is Ph-$CH_2$—, and $R^4$ is Ph-$CH_2$—.

17. A process as in claim 12, wherein $R^1$ is alkyl, $R^2$ is alkyl, $R^3$ is Ph-$CH_2$—, $R^4$ is Ph-$CH_2$—, and said $R^3$dialkylsilyl halide is $BnMe_2SiCl$.

18. A process as in claim 17, wherein said reacting said alkenyllithium species with a $R^3$dialkylsilyl halide comprises reacting with from about 1.5 to about 2.0 equivalents of $BnMe_2SiCl$.

19. A process as in claim 12, further comprising transforming said compound of formula (I) into a salt.

20. A process as in claim 12, further comprising transforming said compound of formula (I) into a hydrochloride salt.

21. A process as in claim 18, further comprising transforming said compound of formula (I) into a salt.

22. A process as in claim 20, further comprising cross-coupling said salt with an organo halide.

23. A process as in claim 22, wherein said organo halide is an aryl iodide.

24. A process as in claim 22, wherein said organo halide is an aryl bromide.

25. The compound obtained by the process of claim 22.

26. The compound obtained by the process of claim 23.

27. The compound obtained by the process of claim 24.

28. The compound obtained by the process of claim 16.

29. The compound obtained by the process of claim 18.

* * * * *